United States Patent [19]

Psarras

[11] 4,181,679

[45] Jan. 1, 1980

[54] ω-IODOPERFLUOROALKYLENE OXIDE ACYL FLUORIDES

[75] Inventor: Theodore Psarras, Gainesville, Fla.

[73] Assignee: The United States of America as represented by the Secretary of the Air Force, Washington, D.C.

[21] Appl. No.: 954,943

[22] Filed: Oct. 24, 1978

[51] Int. Cl.$^2$ .................. C07C 53/20; C07C 51/58
[52] U.S. Cl. ................................................ 260/544 F
[58] Field of Search ................. 260/544 F; 260/543 F

[56] References Cited

U.S. PATENT DOCUMENTS 3,862,971  1/1975  Rudolph et al. ................. 260/408

*Primary Examiner*—Gerald A. Schwartz
*Attorney, Agent, or Firm*—Joseph E. Rusz; Cedric H. Kuhn

[57] ABSTRACT

ω-Iodoperfluoroalkylene oxide acyl fluorides are prepared by reacting a perfluoroalkylene oxide α,ω-diiodide with fuming sulfuric acid in the presence of zinc sulfate. The iodoacyl fluorides are intermediates for use in synthesizing perfluoroalkylene ether diimidate esters.

4 Claims, No Drawings

ω-IODOPERFLUOROALKYLENE OXIDE ACYL FLUORIDES

RIGHTS OF THE GOVERNMENT

The invention described herein may be manufactured and used by or for the Government of the United States for all governmental purposes without the payment of any royalty.

FIELD OF THE INVENTION

This invention relates to ω-iodoperfluoroalkylene oxide acyl fluorides. In one aspect it relates to a process for preparing the iodoacyl fluorides.

BACKGROUND OF THE INVENTION

The iodoacyl fluoride $CF_2ICF_2OCF_2COF$ can be prepared by the addition of tetrafluoroethylene to a mixture of oxalyl fluoride, potassium fluoride and iodine monochloride. The addition of tetrafluoroethylene oxide (TFEO) to the aforementioned iodoacyl fluoride can be represented by the following equation:

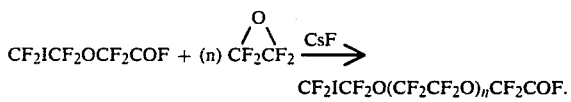

In this reaction, the TFEO take-up is slow, and the reaction leads to a broad distribution of oligomers. Hence, it is unsuitable for the production of a given oligomer that is useful as a monomeric material.

U.S. Pat. No. 3,862,971 discloses a process for preparing perfluorinated carboxylic acids and their fluorides. In accordance with this process a fluoroalkyl iodide of the formula $R_f(CF_2CF_2)_nI$, where $R_f$ is perfluoroalkyl, is reacted with oleum in the presence of a metal salt while adding chlorine.

A great deal of research work has been performed with the view of providing monomers that can be used in the synthesis of elastomeric polymers suitable for various aerospace applications. Because of their outstanding thermal, oxidative and chemical stability, much of the work has been directed toward the preparation of fluorocarbon polymers for use in aerospace seal and sealant applications Iodoacyl fluorides are important intermediates for use in the synthesis of monomers for employment in preparing elastomeric polymers which are useful for such applications. It would be desirable to have a process for preparing ω-iodoperfluoroalkylene oxide acyl fluorides that can be used in the synthesis of a given oligomer.

It is an object of this invention, therefore, to provide a process for preparing specific ω-iodoperfluoroalkylene oxide acyl fluorides.

Another object of the invention is to provide intermediates for use in the synthesis of monomeric materials to be used in preparing elastomeric polymers.

Other objects and advantages of the invention will become apparent to those skilled in the art upon consideration of the accompanying disclosure.

SUMMARY OF THE INVENTION

The present invention resides in a process for preparing ω-iodoperfluoroalkylene oxide acyl fluorides. In accordance with the process, a perfluoroalkylene oxide having the following formula:

$$CF_2ICF_2O(CF_2)_xOCF_2CF_2I,$$

where x is an integer equal to at least 2, e.g., an integer in the range of 2 to 10, inclusive, is reacted with fuming sulfuric acid in the presence of zinc sulfate. The reaction involved in carrying out the process can be represented by the following equation:

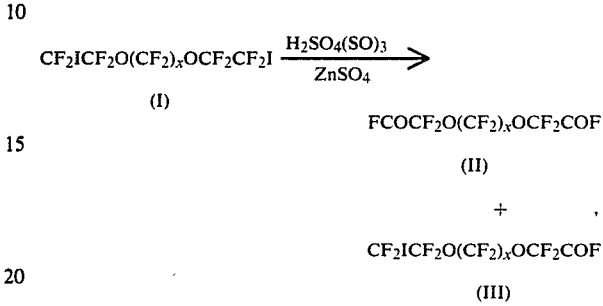

where x is as defined above. The iodoacyl fluoride (III), the product of this invention, is separated from the diacyl fluoride (II) by fractional distillation.

In a preferred procedure for conducting the present process, a mixture of the perfluoroalkylene oxide α,ω-diiodide (I) and the zinc sulfate catalyst is heated at a temperature in the range of about 60° to 120° C. The fuming sulfuric acid is then added to the mixture at a rate such as to maintain the reaction temperature in the range of about 100° to 120° C. The duration of the reaction period will vary with the diiodide employed, but it usually ranges from about 4 to 24 hours. Upon completion of the sulfuric acid addition, the reaction mixture is generally heated at a temperature ranging from about 100° to 120° C. for a period of about 1 to 2 hours. At the end of the reaction period, the ω-iodoacyl fluoride is separated from the reaction mixture by fractional distillation.

The fuming sulfuric acid generally contains about 65 weight percent free sulfur trioxide. However, it is to be understood that fuming sulfuric acid containing other concentrations of free $SO_3$ can be utilized. In general, a molar excess of free $SO_3$ as compared to diiodide (I) is employed. Thus, the mole ratio of free $SO_3$ to diiodide (I) usually ranges from about 10 to 150:1.

In general, a catalytic amount of zinc sulfate is used in the process. While the actual amount employed can vary over a relatively wide range, the amount is usually in the range of about 1 to 20 weight percent, based upon the weight of the diiodide (I).

The diiodide (I) used in the process is prepared by addition of tetrafluoroethylene to a mixture of an acyl fluoride, potassium fluoride and iodine monochloride. The acyl fluorides can be represented by the formula $FCO(CF_2)_{x-2}COF$, where x is an integer equal to at least 2, e.g., an integer ranging from 2 to 10, inclusive. Examples of the acyl fluorides include oxalyl difluoride and difluorides of perfluoromalonic acid, perfluorosuccinic acid, perfluoroglutaric acid, perfluoroadipic acid, perfluoropimelic acid, perfluoroazelaic acid, perfluorosebacic acid, and the like.

In a preferred procedure for preparing the diiodide (I), potassium fluoride is initially dried in an appropriate reaction vessel at an elevated temperature under vacuum. After cooling to room temperature, the acyl fluoride and a solvent, such as diglyme, are charged to the vessel. The resulting mixture is stirred until the exothermic reaction subsides and most of the potassium fluoride is dissolved. The mole ratio of potassium fluoride to acyl fluoride is generally at least 2 to 1. The reaction mixture is then cooled in an ice bath after which the iodine monochloride is added. The mole ratio of iodine monochloride to acyl fluoride is also usually at least 2 to 1. After allowing the mixture to warm to room temperature while stirring, the reaction vessel is connected to a tetrafluoroethylene cylinder. Tetrafluoroethylene is then pressured into the vessel until the rate of take-up is negligible. Excess tetrafluoroethylene is vented and the reaction mixture is distilled to give the diiodide (I).

As mentioned above, the addition of tetrafluoroethylene oxide to the iodoacyl fluoride $CF_2ICF_2OCF_2COF$ can be represented by the following formula:

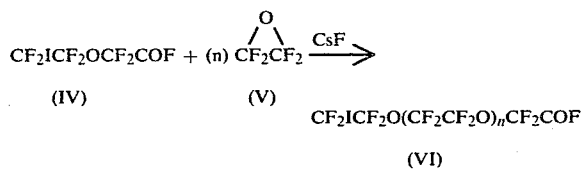

(IV)   (V)

$$CF_2ICF_2O(CF_2CF_2O)_nCF_2COF$$

(VI)

Because of the broad distribution of products obtained, this process is incapable of producing a particular oligomer. However, by sibstituting the ω-iodoacyl fluoride (III) of this invention for the iodoacyl fluoride (IV) shown in the foregoing equation, it is possible to synthesize a given oligomer. Since the oligomers or their derivatives are intended primarily for use as monomers in polymerization reactions, it is, of course, very desirable to have available a process for preparing the pure monomers. The reaction involved in the addition of tetrafluoroethylene oxide to the ω-iodoacyl fluorides of this invention is shown by the following equation:

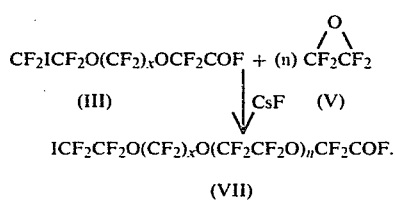

$$ICF_2CF_2O(CF_2)_xO(CF_2CF_2O)_nCF_2COF.$$

(VII)

In the foregoing equation, x is as indicated above and n is an integer equal to at least 1, e.g., an integer ranging from 1 to 10, inclusive. The reaction is conducted in the presence of a catalytic amount of cesium fluoride in a solvent, such as tatraglyme, at subzero temperatures, e.g., at a temperature in the range of about $-20°$ C. to $-10°$ C.

The ω-iodoperfluoroalkylene oxide acyl fluorides are particularly useful as intermediates for synthesizing perfluoroalkylene ether diimidate esters. The latter compounds are useful as monomers in preparing perfluoroalkylene ether bibenzoxazole polymers. It is generally preferred to utilize ω-iodoacyl fluoride (VII) rather than ω-iodoacyl fluoride (III) as a starting material because of the higher oxygen/carbon ratio of the former oligomers. A high oxygen/carbon ratio in the monomer ensures a greater flexibility of the final polymeric product, generally manifested as a lower glass transition temperature.

In preparing the imidate esters, the ω-iodoacyl fluoride is initially esterified with methanol to obtain the ω-ester perfluoroalkylene oxide iodide. Thereafter, in a four-step procedure, the iodoester is converted to a diimidate ester. In the first step, the iodoester is reacted with particulate zinc metal to form a diester. The reaction is conducted in acetic anhydride and 1,1,2-trifluorotrichloroethane under reflux conditions and in an inert atmosphere. In the second step, ammonia is bubbled through an ether-1,1,2-trifluorotrichloroethane solution of the diester recovered from the first step to form a diamide product. The diamide product recovered from the second step is mixed and heated with phosphorus pentoxide in the third step to provide a dinitrile. In the final and fourth step, the dinitrile recovered from the third step is added to a solution of sodium in methanol. In the reaction that occurs, the diimidate ester is formed. For a more detailed discussion of the preparation of the diimidate esters, reference may be made to U.S. Pat. No. 4,011,255.

The diimidate esters, prepared as described above using ω-iodoacyl fluorides as starting materials, are reacted with fluorocarbon ether bis(o-aminophenol) monomers to provide linear fluorocarbon ether bibenzoxazole polymers. Examples of fluorocarbon ether bis(o-aminophenols) include 1,11-bis(3-amino-4-hydroxyphenyl)-perfluoro-3,9-dioxaundecane, 1,14-bis(3-amino-4-hydroxyphenyl)perfluoro-5,10-dimethyl-3,6,9,12-tetraoxatetradecane, and 1,17-bis(3-amino-4-hydroxyphenyl)-perfluoro-3,6,9,15-tetraoxaheptadecane. The polymers are elastomeric, have a low glass transition temperature, and are oxidatively stable at elevated temperatures. The polycondensation reaction is generally conducted in hexafluoroisopropanol at about 50° to 55° C. in the presence of four molar equivalents of glacial acetic acid.

A more comprehensive understanding of the invention can be obtained by referring to the following illustrative examples which are not intended, however, to be unduly limitative of the invention.

EXAMPLE I

Preparation of $CF_2ICF_2OCF_2CF_2OCF_2CF_2I$

Potassium fluoride (55 g, 1.0 mole) was charged to a Fischer-Porter pressure bottle containing a magnetic stirring bar and dried over night at 200° C. under vacuum. After the bottle was cooled to room temperature, tetraglyme (200 ml) was added and the mixture was stirred for a few minutes under vacuum. The reaction vessel was cooled in a Dry Ice-acetone bath and oxalyl fluoride (FCOCOF) (48 g, 0.48 mole) was charged through a vacuum manifold. The mixture was allowed to warm up to ambient temperature and was stirred for one hour. The reaction vessel was cooled in a Dry Ice-acetone bath, iodine monochloride (50 ml, 1.0 mole) was added through a syringe, and the system was evacuated. The reaction vessel was connected through copper tubing to a cylinder of tetrafluoroethylene (TFE), and the mixture was allowed to reach room temperature. The stirrer was turned on and TFE was pressured in at 35 psi. After several days, the reaction was terminated when the deep red color of the reaction mixture had turned to a light yellow color. The excess of TFE and volatile products were vented, and the reaction mixture was poured into water. After the iodine was destroyed with a solution of sodium bisulfite, the product was separated as the heavy phase. The crude products of several runs were combined and distilled on an Oldershaw column. The average yield of the diiodide (b.p. 60°–61° C./13 mm) was 16 percent.

EXAMPLE II

Preparation of CF$_2$ICF$_2$O(CF$_2$)$_5$OCF$_2$CF$_2$I

Potassium fluoride (25 g, 0.43 mole) was charged to a Fischer-Porter pressure bottle and dried over night at 200° C. under vacuum. After cooling to room temperature, diglyme (200 ml) and hexafluoroglutaryl fluoride (HFGF) [FCO(CF$_2$)$_3$COF] (46 g, 0.19 mole) were charged to the bottle and the resulting mixture was stirred for one hour. At the end of this period, the exothermic reaction had subsided and most of the potassium fluoride had been dissolved. The reaction mixture was cooled in an ice bath and iodine monochloride (26 ml, ≃0.5 mole) wad added through a syringe. The mixture was stirred and allowed to warm to room temperature.

The bottle was connected to a tetrafluoroethylene (TFE) cylinder through copper tubing and TFE was pressured in at 60 psi. The progress of the reaction was followed by the drop in pressure and more TFE was added until the take-up rate was negligible. At this point the color of the reaction mixture had changed to light pink yellow from the originally deep red color. After excess TFE was vented, the reaction mixture was poured into water and decolorized with Na$_2$S$_2$O$_3$. The crude product was separated as the heavy phase. The crude product was washed repeatedly with a 5% solution of NaHCO$_3$, dried and distilled.

Several runs were made in accordance with the foregoing procedure, using a total of 440 g (1.8 moles) of HFGF. Distillation gave the diiodide (99.8% purity) in 36.7% average conversion.

EXAMPLE III

Preparation of CF$_2$ICF$_2$OCF$_2$CF$_2$OCF$_2$COF

The diiodide CF$_2$ICF$_2$OCF$_2$CF$_2$OCF$_2$CF$_2$I (0.6 mole), prepared as described in Example I, and ZnSO$_4$ (6 g) were added to a three-neck flask equipped with thermometer relux condenser, magnetic stirrer, dropping funnel and gas inlet tube. The mixture was heated at 90° C. and fuming sulfuric acid (1070 g, 65% SO$_3$) was added over a period of 6 hours. An exothermic reaction ensued and the rate of addition of sulfuric acid was regulated so as to maintain the reaction temperature at 100°-120° C. After the addition of sulfuric acid was completed, the mixture was heated at this temperature for an additional 75 minutes. GLC analysis at this point showed the following composition: FCOCF$_2$OCF$_2$CF$_2$OCF$_2$COF (21.7%); CF$_2$ICF$_2$OCF$_2$CF$_2$OCF$_2$COF (35%); and unreacted diiodide (37.7%).

The reaction mixture was heated at 85°-90° C. for an additional 4 hours at which point the product had the following composition: FCOCF$_2$OCF$_2$CF$_2$OCF$_2$CFO (52%); CF$_2$ICF$_2$OCF$_2$CF$_2$OCF$_2$COF (26.3%); and unreacted diiodide (7%).

EXAMPLE IV

Preparation of CF$_2$ICF$_2$O(CF$_2$)$_5$OCF$_2$COF

A run is conducted in which fuming sulfuric acid (65% SO$_3$) is added to a mixture of the diiodide CF$_2$ICF$_2$O(CF$_2$)$_5$OCF$_2$CF$_2$I, prepared as described in Example II, and ZnSO$_4$. A molar excess of sulfuric acid as compared to the diiodide is added, and the reaction temperature is controlled in substantially the same manner as described in Example III. At the end of the reaction period, the ω-iodoacylfluoride is separated from the reaction mixture by distillation.

As seen from the foregoing, the present invention provides a process for preparing ω-iodoperfluoroalkylene oxide acyl fluorides. The data indicate that the product yield can be controlled by varying the period during which the diiodide starting material is reacted with the fuming sulfuric acid. The ω-iodoacyl fluorides are particularly useful as starting materials for preparing oligomers which are used as monomers in the synthesis of bibenzoxazole polymers. Because they are thermally stable and have a low glass transition temperature, the polymers are eminently suitable for various aerospace applications, such as for seals and sealants.

As will be evident to those skilled in the art, various modifications of the present invention can be made in view of the foregoing disclosure without departing from the spirit and scope of the invention.

I claim:

1. A process for preparing ω-iodoperfluoroalkylene oxide acyl fluorides which consists of the steps of heating a mixture consisting of a diiodide and a catalytic amount of zinc sulfate at a temperature in the range of about 60° to 120° C., the diiodide having the following formula:

CF$_2$ICF$_2$O(CF$_2$)$_x$OCF$_2$CF$_2$I, where x is an integer equal to at least 2; adding only fuming sulfuric acid to the mixture at a rate such as to maintain a reaction temperature in the range of about 100° to 120° C.; and recovering from the mixture an iodoacyl fluoride having the following formula:

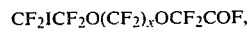

CF$_2$ICF$_2$O(CF$_2$)$_x$OCF$_2$COF, where x is an integer equal to at least 2.

2. The process according to claim 1 in which the reaction mixture is maintained at a temperature in the range of about 100 to 120° C. for a period of about 4 to 24 hours and upon completion of the sulfuric acid addition the reaction mixture is heated at a temperature in the range of about 100° to 120° C. for a period of about 1 to 2 hours.

3. The process according to claim 2 in which x is an integer in the range of 2 to 10, inclusive.

4. The process according to claim 3 in which the mole ratio of sulfur trioxide contained in the fuming sulfuric acid to the diiodide ranges from about 10 to 150:1, and the amount of zinc sulfate ranges from about 1 to 20 weight percent, based upon the weight of the diiodide.

* * * * *